(12) United States Patent
Clevenger et al.

(10) Patent No.: US 9,868,808 B2
(45) Date of Patent: Jan. 16, 2018

(54) QUATERNARY PHOSPHONIUM COATED SURFACES AND METHODS OF MAKING THE SAME

(71) Applicant: Orthobond, Inc., North Brunswick, NJ (US)

(72) Inventors: Randy Clevenger, North Plainfield, NJ (US); Se-Ho Kim, North Brunswick, NJ (US)

(73) Assignee: Orthobond, Inc., North Brunswick, NJ (US)

( * ) Notice: Subject to any disclaimer, the term of this patent is extended or adjusted under 35 U.S.C. 154(b) by 156 days.

(21) Appl. No.: 14/922,983

(22) Filed: Oct. 26, 2015

(65) Prior Publication Data

US 2016/0115268 A1    Apr. 28, 2016

Related U.S. Application Data

(60) Provisional application No. 62/068,347, filed on Oct. 24, 2014.

(51) Int. Cl.
*C08F 292/00*    (2006.01)
(52) U.S. Cl.
CPC ........ *C08F 292/00* (2013.01); *C08F 2438/01* (2013.01)
(58) Field of Classification Search
CPC ........................... C08F 292/00; C08F 2438/01

USPC ........................................................ 526/274
See application file for complete search history.

(56) References Cited

U.S. PATENT DOCUMENTS

| | | |
|---|---|---|
| 7,759,401 B2 | 7/2010 | Yan |
| 2002/0102405 A1 | 8/2002 | Chapman et al. |
| 2003/0225189 A1 | 12/2003 | Fuller |
| 2005/0106576 A1* | 5/2005 | Akhavan-Tafti ....... C07H 21/04 435/6.16 |
| 2008/0138626 A1 | 6/2008 | Denes |
| 2008/0226585 A1 | 9/2008 | Bouloussa et al. |
| 2010/0136353 A1 | 6/2010 | Schellekens et al. |
| 2010/0215643 A1 | 8/2010 | Clevenger et al. |
| 2010/0291169 A1 | 11/2010 | Toreki et al. |
| 2013/0101677 A1 | 4/2013 | Callahan et al. |

OTHER PUBLICATIONS

International Search Report and Written Opinion for International Patent Application No. PCT/US15/57374, dated Jan. 14, 2016, 14 pgs.

* cited by examiner

*Primary Examiner* — Ling Choi
*Assistant Examiner* — Chun-Cheng Wang
(74) *Attorney, Agent, or Firm* — Lowenstein Sandler LLP

(57) ABSTRACT

Disclosed herein is a composition comprising a substrate with functionalized surface covalently bound to an anti-infective agent, such as a quaternary phosphonium compound with anti-bacterial activity against a broad range of bacteria, methods of synthesizing an anti-infective composition, and its resultant antimicrobial performance.

16 Claims, 6 Drawing Sheets

QUATERNARY PHOSPHONIUM COATED SURFACES AND METHODS OF MAKING THE SAME

CROSS-REFERENCE TO RELATED APPLICATIONS

This application claims the benefit of U.S. Provisional Patent Application Ser. No. 62/068,347, filed Oct. 24, 2014, the entirety of which is incorporated herein by reference.

FIELD OF THE INVENTION

The present invention relates to surface attachment of quaternary phosphonium compounds with anti-bacterial activity against a broad range of bacteria. In particular, methods are provided for attaching various substrate surfaces to quaternary phosphonium compounds to obtain anti-bacterial activity.

BACKGROUND OF THE INVENTION

The need for control of infection is a vital concern for many, from public health officials, hospital and school administrators and the like, to private citizens. Typically, control of infection can be achieved by the topical application of disinfectants, antiseptics, antibacterials and the like to surfaces likely to be contacted by infectious agents. Common disinfectants include active chlorine such as hypochlorites, chloramines, dichloroisocyanurate and trichloroisocyanurate, wet chlorine, chlorine dioxide and the like, active oxygen, including peroxides, such as peracetic acid, potassium persulfate, sodium perborate, sodium percarbonate and urea perhydrate, iodine compounds such as povidone iodide, iodine tincture, iodinated nonionic surfactants, concentrated alcohols such as ethanol, n-propanol and isopropanol and mixtures thereof; 2-phenoxyethanol and 1- and 2-phenoxypropanols, phenolic compounds, cresols, halogenated phenols, such as hexachlorophene, triclosan, trichlorophenol, tribromophenol, pentachlorophenol, Dibromol and salts thereof, cationic surfactants, including quaternaryammonium cations such as benzalkonium chloride, cetyl trimethylammonium bromide orchloride, didecyldimethylammonium chloride, cetylpyridinium chloride, benzethonium chloride and others, and non-quaternary compounds, such as chlorhexidine, glucoprotamine, octenidine dihydrochloride etc.); strong oxidizers, such as ozone and permanganate solutions; heavy metals and their salts, such as colloidal silver, silver nitrate, mercury chloride, phenylmercury salts, copper, copper sulfate, copper oxide-chloride and the like, and strong acids (phosphoric, nitric, sulfuric, amidosulfuric, toluenesulfonic acids) and alkalis (sodium, potassium, calcium hydroxides). However, many of these compounds are harmful to mammalian tissue. Moreover, these compounds only have a short-term effect resulting in a need to be reapplied constantly.

Antibiotics can be administered to stop infection in individuals. However, such administration is not always effective. Numerous medical applications, including orthopedic, trauma, spine and general surgery applications, where the potential for infection is a serious concern, are not amenable to simple application of antiseptic or treatment with antibiotics. For example, infection can be a devastating complication of a total joint arthroplasty (TJA). While some infections may be treated by antibiotic suppression alone, more aggressive therapies, such as two-stage re-implantation, are often required. The treatment of post-arthroplasty infections in 1999 cost over $200 million in the US alone. Spangehl, M. J., et al., *J Bone Joint Surg. Am.*, 1999, 81(5), 672-682. TJA infections occur when bacteria colonize the surface of the implant. These species then form a resistant biofilm on the implant surface, which nullifies the body's normal antibody response.

External fixation devices provide temporary but necessary rigid constraints to facilitate bone healing. However, patients risk pin-tract infection at the site extending from the skin-pin interface to within the bone tissue. Such complications can result in sepsis and osteomyelitis, which could require sequestrectomy for correction. Even the most stringent pin-handling and post-procedure protocols have only a limited effect. Studies have shown that such protocols do not reduce the chance of infection. Davies, R., et al. *J Bone Joint Surg. Br.,* 2005, 87-B, 716-719.

In minimally-invasive spine fusions, pedicle screws are first implanted in the bone of the vertebrae, and then rods are fixed into the heads of the screws to immobilize and stabilize the affected segments. Screws and rods pass through the patient's skin into the spine space via a cannulated channel. As in external fixation, screws and rods are also prone to pin-tract infections; due to the implants' pathway through the skin, the chance of contacting and/or passing harmful bacteria is greatly increased.

Catheters and shunts are placed in any number of body cavities and vessels to facilitate the injection, drainage, or exchange of fluids. Infections are common in catheter placements and are largely dependent on how long the patient is catheterized. For example, Kass reports an infection rate of virtually 100% for patients with indwelling urethral catheters draining into an open system for longer than 4 days. Kass, E. H., *Trans. Assoc. Am. Physicians,* 1956, 69, 56-63.

Therefore, there is a need for substrates and materials with anti-infective surfaces, such as medical devices including implants, screws, rods, pins, catheters, stents, surgical tools and the like which could prevent infections by proactively killing bacteria that attempt to colonize the device surface both pre- and post-operatively. Moreover, there is a need for anti-infective surfaces that may be employed in locations particularly susceptible to hosting infectious agents, such as public places, common areas of buildings, fixtures and the like.

SUMMARY OF THE INVENTION

In some embodiments of the invention, a surface of interest is functionalized in accordance with a suitable functionalization method and an anti-infective agent is disposed on the functionalized surface.

In some embodiments, the invention is directed to a composition comprising a substrate comprising a functionalized surface and a quaternary phosphonium compound covalently bound directly to the functionalized surface.

In some embodiments the surface of the substrate is functionalized with a functionalizing agent. In other embodiments the surface of the substrate may be natively functionalized.

In some embodiments a linker, having a proximal and a distal end, may be covalently bound on its proximal end to the functionalized surface of the substrate, and may be covalently bound on its distal end to a quaternary phosphonium compound.

In some embodiments a plurality of linkers may be covalently bound on their proximal ends to the functionalized surface or to a plurality of functionalizing agents, with each linker being covalently bound on their distal end to a plurality of anti-infective agents. In some embodiments, the anti-infective agents may be all the same, for example, quaternary phosphonium compounds. In other embodiments, the anti-infective agents may vary, for example, various quaternary phosphonium compounds, or a combination of quaternary phosphonium compounds with other anti-infective agents. In some embodiments, the plurality of functionalizing agents is independently identical or different. In some embodiments, the plurality of linkers is independently identical or different.

In some embodiments, the composition may take a form of an antibacterial polymer brush comprising a surface and a thickness. In some embodiments, varying antibacterial polymer brush thickness may have varying antibacterial efficacy. In some embodiments, the antibacterial polymer brush disrupts bacterial cells, thereby maintaining antibacterial activity for prolonged duration without being reapplied.

In some embodiments, the anti-infective agent may be a quaternary phosphonium compound having the radical formula of formula I:

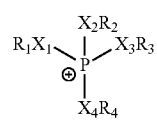

Formula I wherein $X_1$, $X_2$, $X_3$, and $X_4$ are independently non-existent or independently selected from O, S, $NR_5$, $=N-$, $PR_6$, and $=P-$, and wherein $R_1$, $R_2$, $R_3$, $R_4$, $R_5$, and $R_6$ are independently selected from the group consisting of hydrogen, alkyls, substituted alkyl, cycloalkyl, substituted cycloalkyl, cycloalkenyl, substituted cycloalkenyl, alkenyl, substituted cycloalkenyl, alkynyl, substituted alkynyl, haloalkyl, hydroxyalkyl, alkoxy, alkoxyalkyl, heteroalkyl, haloalkoxy, aryl, substituted aryl, aryloxy, aralkyloxy, heteroaryl, substituted heteroaryl, heterocycle, substituted heterocycle, amino, alkylamino, dialkylamino, hydroxyalkylamino, (amino)alkyl, (alkylamino)alkyl, (dialkylamino)alkyl, (cyano)alkyl), carboxamido, (carboxamido)alkyl, methacrylate, methacrylamide, sulfonamide, alkylcarbonyl, arylcarbonyl, alkylsulfonyl, arylsulfonyl, mercaptoalkyl, carboxy, carboxyalkyl, ureido, guanidine, (heterocyclo)alkyl, (heteroaryl)alkyl.

In some embodiments, one of $R_1$, $R_2$, $R_3$, or $R_4$ may bind the quaternary phosphonium compound either directly to the functionalized surface, functionalizing agent, or to the distal end of a linker. In other embodiments, more than one of $R_1$, $R_2$, $R_3$, or $R_4$ may bind the quaternary phosphonium compound either directly to a functionalized surface, to a functionalizing agent, or to the distal end of a linker. In some embodiments, $R_1$, $R_2$, $R_3$ and $R_4$ may be the same. In other embodiments, some of $R_1$, $R_2$, $R_3$ and $R_4$ may be the same and some may be different.

Virtually any surface which may be functionalized is suitable for the inclusion of an anti-infective agent in accordance with the disclosed embodiments. Examples of such surfaces include but are not limited to metals, alloys, polymers, plastics, ceramics, silicon, glass, composites, tissue and surfaces with acidic protons.

Functionalization of substrates in accordance with the present invention may be achieved in a variety of ways. For example, the surfaces of the substrates can be functionalized by a reaction with functionalizing agents such as phosphonic acids, phosphoric acids, carboxylic acids, sulfonic acids, sulfinic acids, phosphonates, phosphonic acid anhydrides, phosphoric acid esters, phosphorus pentoxides, carboxylic acid esters, carboxylic anhydrides, sulfonates, sulfonic acid anhydrides, sulfinic esters, sulfinic anhydrides, alcohols, thiols, alkanes, alkenes, alkynes, and diazo compounds. In some embodiments, the surfaces may be naturally functionalized.

Anti-infective agents as discussed herein may include bactericidal and bacteriostatic agents including disinfectants, antiseptics and antibiotics. Not all bactericidal and bacteriostatic agents may be used as antiseptics on mammalian tissue as they may have adverse effects thereon. Some embodiments of the present invention may involve uses without contact of an anti-infective surface with mammalian tissue, such as interior surfaces of plumbing fixtures, building materials, ductwork, clean rooms, etc. In such applications certain anti-infective agents may be used, such as disinfectants, which would not be appropriate for use in applications in which contact with mammalian tissue was contemplated or possible.

In other embodiments, the anti-infective composition of the present invention may involve contact with mammalian tissue and may comprise quaternary ammonium compounds such as choline and choline derivatives, quaternary ammonium dendrimers, silver, copper, and cationic species; silver and copper. In other embodiments anti-infective agents may comprise quaternary phosphonium compounds such as phosphonium methacrylate.

Devices made in accordance with the present disclosure provide a multitude of clinical benefits. For example, in partially external devices, anti-infective surfaces thereof may kill bacterial species at the device-skin interface, thus preventing pin-site infections. Devices including an anti-infective surface may prevent the colonization by infectious species of implanted surfaces, potentially reducing the incidence of deep infection, especially in high-risk populations. In catheters and shunts with anti-infective surfaces the potential for infection is minimized by killing bacteria traveling up the intubated pathway into the patient. Another example is in total hip arthroplasties; anti-infective hip stems may kill bacterial species and inhibit biofilm formation at the device-tissue interface, preventing the bacterial colonization of the hip replacement, which can lead to loosening due to infection and could require cost and painful hip revision surgery. The anti-infective agent is highly stable under physiological conditions. The anti-infective agent does not leach from its material host, so there is no undesirable secondary result. Due to its nanometer scale, the anti-infective agent does not interfere with desired mechanical surface features that may be critical to the function of device such as an implant. The anti-infective agent is not visible to the naked eye and does not obscure identifying features or product markings.

Devices in accordance with the present disclosure are not limited to medical devices. For example, devices embodying the present disclosures may include fixtures, structures, fittings, barriers, and the like having anti-infective surfaces.

In some embodiments, the invention is directed to a method of making an anti-infective composition, the method comprising covalently binding an anti-infective agent to a functionalized surface of a substrate.

In some embodiments, the method comprises covalently binding a quaternary phosphonium compound either directly to a functionalized surface, to a functionalizing agent, or to a distal end of a linker which is covalently bonded to the functionalized surface or to a functionalizing agent.

In some embodiments, a linker is initially covalently bound on its proximal end to a functionalized surface and an anti-infective agent, such as a quaternary phosphonium compound, is subsequently covalently bound to the linker's distal end. In other embodiments, a linker is initially covalently bound on its distal end to an anti-infective agent, such as a quaternary ammonium compound, and is subsequently covalently bound on its proximal end to the functionalized surface.

In some embodiments, the anti-infective agent, e.g. quaternary phosphonium compound, may be activated before covalently binding it to a functionalized surface, a functionalizing agent, or a linker's distal end. In some embodiments, the functionalized surface may be activated before covalently binding it to a linker's proximal end or to an anti-infective agent.

In some embodiments, the covalent binding may be performed through surface initiated atom transfer radical polymerization.

In some embodiments, after the linker is covalently bound on one of its ends, either on the proximal end to the functionalized surface or on the distal end to the anti-infective agent, it is polymerized pursuant to predetermined parameters, such as time and amount of monomer, thereby obtaining a polymer brush structure with a desired surface and thickness. In some embodiments, after polymerization of the linker is complete, the unbound end of the linker (either distal or proximal) is covalently bound to either the functionalized surface or the anti-infective agent. In some embodiments, varying polymer brush thickness may result in varying antimicrobial activity.

BRIEF DESCRIPTION OF THE DRAWINGS

The above and other features of the present disclosure, their nature, and various advantages will become more apparent upon consideration of the following detailed description, taken in conjunction with the accompanying drawings, in which.

DETAILED DESCRIPTION OF THE PREFERRED EMBODIMENTS

Figure 1:
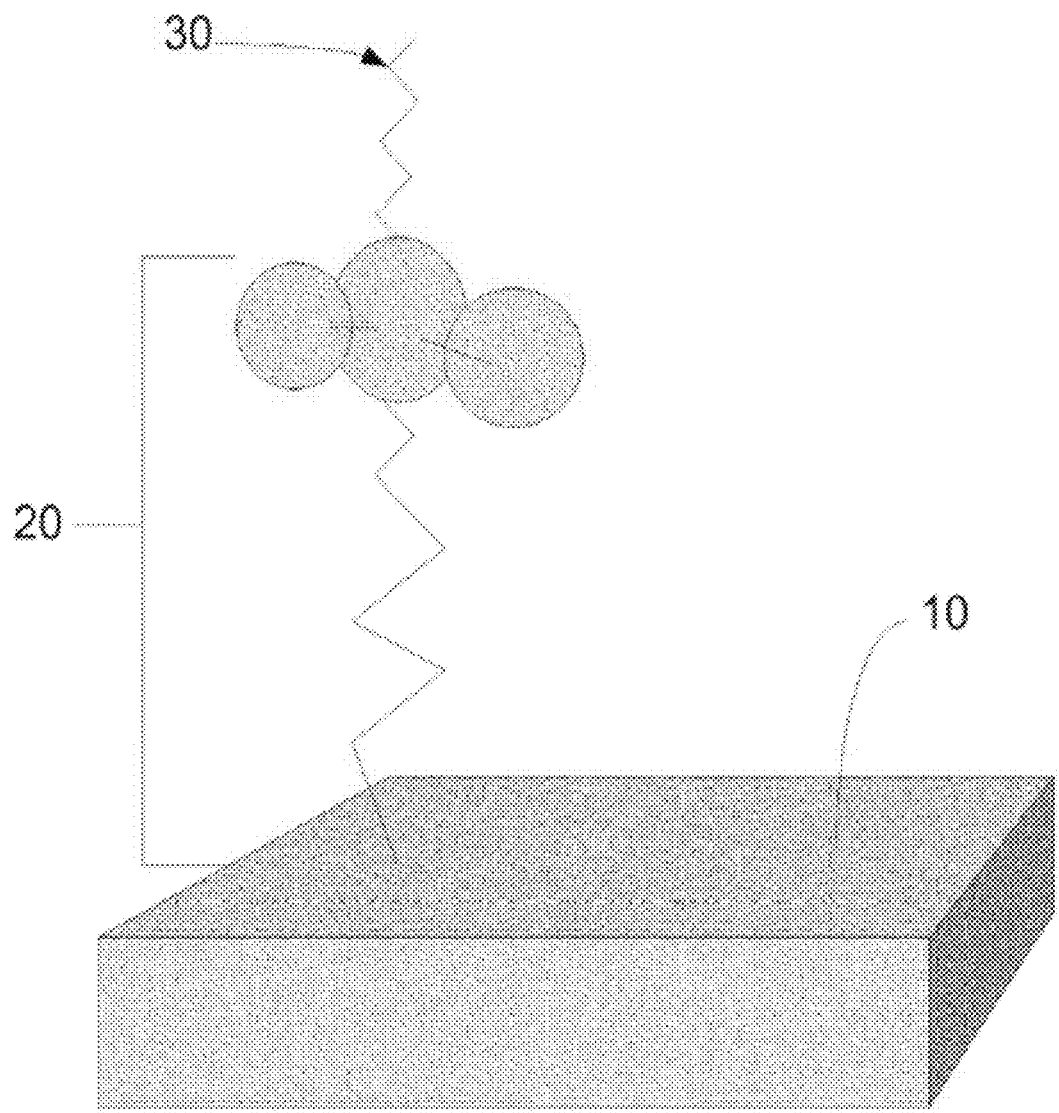
FIG. 1 depicts a schematic of an anti-infective agent bound to a surface in accordance with at least one embodiment of the present disclosure.

For the purpose of the present disclosure, the term "alkyl" as used by itself or as part of another group refers to a linear or branched chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a linear chain $C_{1-10}$ alkyl group. In another embodiment, the alkyl group is chosen from a branched chain $C_{1-10}$ alkyl group. In another embodiment, the alkyl group is chosen from a linear chain $C_{1-6}$ alkyl group. In another embodiment, the alkyl group is chosen from a branched chain $C_{1-6}$ alkyl group. In another embodiment, the alkyl group is chosen from a linear chain $C_{1-4}$ alkyl group. In another embodiment, the alkyl group is chosen from a branched chain $C_{1-4}$ alkyl group. In another embodiment, the alkyl group is chosen from a linear or branched chain $C_{2-4}$ alkyl group. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2CH_2CO_2H$, —$CH_2CH_2SO_2CH_3$, —$CH_2CH_2COPh$, —$CH_2C_6H_{11}$, and the like.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

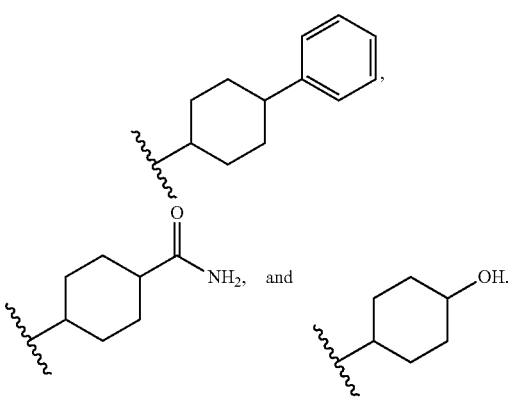

For the purpose of the present disclosure, the term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a $C_{4-8}$ cycloalkenyl group. Exemplary cycloalkenyl groups include cyclopentenyl, cyclohexenyl, and the like.

For the purpose of the present disclosure, the term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl, optionally substituted cycloalkenyl, optionally substituted alkynyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "heteroalkyl" as used by itself or part of another group refers to a stable linear or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include —CH$_2$OCH$_2$CH$_2$OCH$_3$, —OCH$_2$CH$_2$OCH$_2$CH$_2$OCH$_3$, —CH$_2$NHCH$_2$CH$_2$OCH$_2$, —OCH$_2$CH$_2$NH$_2$, and —NHCH$_2$CH$_2$N(H)CH$_3$.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic or bicyclic aromatic ring system having from six to fourteen carbon atoms (i.e., $C_{6-14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include:

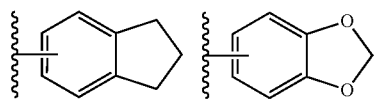

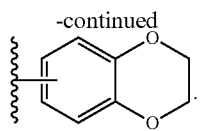

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "aralkyloxy" as used by itself or as part of another group refers to an aralkyl group attached to a terminal oxygen atom. A non-limiting exemplary aralkyloxy group is PhCH$_2$O—.

For the purpose of the present disclosure, the term "heteroaryl" or "heteroaromatic" refers to monocyclic and bicyclic aromatic ring systems having 5 to 14 ring atoms (i.e., $C_{5-14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide, and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heteroaryl has one substituent. In another embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as 2-imidazolidinone and cyclic amide groups such as β-lactam, γ-lactam, δ-lactam and ε-lactam. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, and the like. Substitution may occur on any available carbon or nitrogen atom, and may form a spirocycle. Non-limiting exemplary optionally substituted heterocyclo groups include:

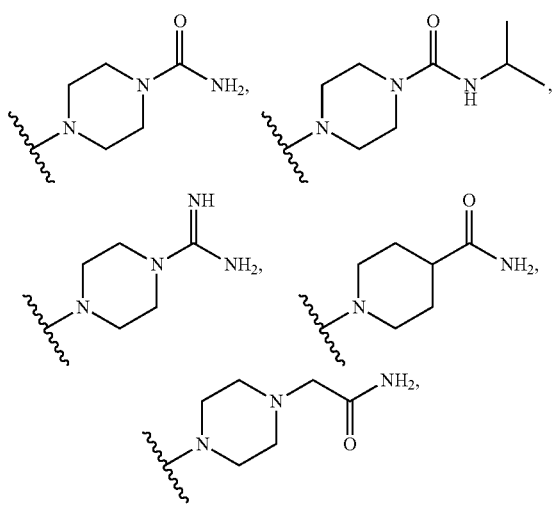

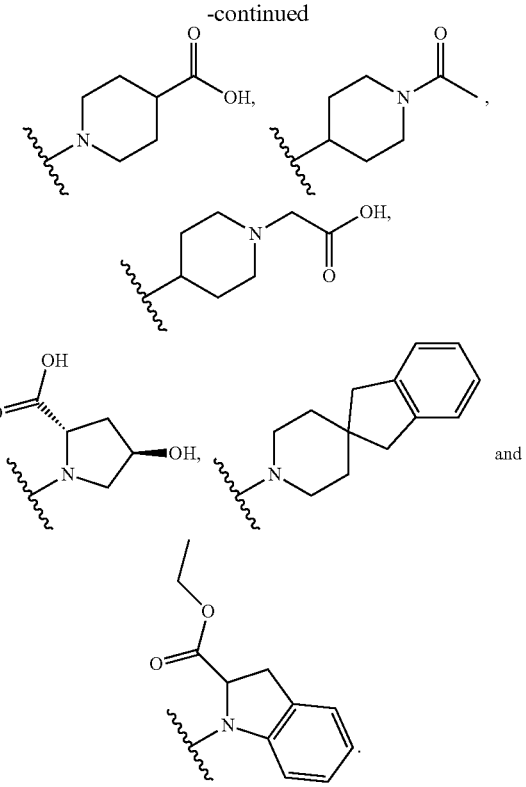

For the purpose of the present disclosure, the term "amino" as used by itself or as part of another group refers to —$NH_2$.

For the purpose of the present disclosure, the term "alkylamino" as used by itself or as part of another group refers to —$NHR^{15}$, wherein $R^{15}$ is alkyl.

For the purpose of the present disclosure, the term "dialkylamino" as used by itself or as part of another group refers to —$NR^{16a}R^{16b}$, wherein $R^{16a}$ and $R^{16b}$ are each independently alkyl or $R^{16a}$ and $R^{16b}$ are taken together to form a 3- to 8-membered optionally substituted heterocyclo.

For the purpose of the present disclosure, the term "hydroxyalkylamino" as used by itself or as part of another group refers to —$NHR^{17}$, wherein $R^{17}$ is hydroxyalkyl.

For the purpose of the present disclosure, the term "(amino)alkyl" as used by itself or as part of another group refers to an alkyl group substituted with an amino group. Non-limiting exemplary amino alkyl groups include —$CH_2CH_2NH_2$, —$CH_2CH_2CH_2NH_2$, —$CH_2CH_2CH_2CH_2NH_2$, and the like.

For the purpose of the present disclosure, the term "(alkylamino)alkyl" as used by itself or as part of another group refers alkyl group substituted an alkylamino group. A non-limiting exemplary (alkylamino)alkyl group is —$CH_2CH_2N(H)CH_3$.

For the purpose of the present disclosure, the term "(dialkylamino)alkyl" as used by itself or as part of another group refers to an alkyl group substituted by a dialkylamino group. A non-limiting exemplary (dialkylamino)alkyl group is —$CH_2CH_2N(CH_3)_2$.

For the purpose of the present disclosure, the term "(cyano)alkyl" as used by itself or as part of another group refers to an alkyl group substituted with one or more cyano, e.g., —CN, groups. Non-limiting exemplary (cyano)alkyl groups include —$CH_2CH_2CN$, —$CH_2CH_2CH_2CN$, and —$CH_2CH_2CH_2CH_2CN$.

For the purpose of the present disclosure, the term "carboxamido" as used by itself or as part of another group refers to a radical of formula —C(=O)NR$^{24a}$R$^{24b}$, wherein R$^{24a}$ and R$^{24b}$ are each independently hydrogen, optionally substituted alkyl, optionally substituted aryl, or optionally substituted heteroaryl, or R$^{24a}$ and R$^{24b}$ taken together with the nitrogen to which they are attached from a 3- to 8-membered heterocyclo group. In one embodiment, R$^{24a}$ and R$^{24b}$ are each independently hydrogen or optionally substituted alkyl. Non-limiting exemplary carboxamido groups include —CONH$_2$, —CON(H)CH$_3$, —CON(CH$_3$)$_2$, and —CON(H)Ph.

For the purpose of the present disclosure, the term "(carboxamido)alkyl" as used by itself or as part of another group refers to an alkyl group with a carboxamido group. Non-limiting exemplary (carboxamido)alkyl groups include —CH$_2$CONH$_2$, —C(H)CH$_3$—CONH$_2$, and —CH$_2$CON(H)CH$_3$.

For the purpose of the present disclosure, the term "methacrylate" as used by itself or as part of another group refers to the radical of formula

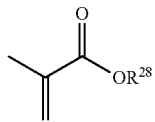

wherein R$^{28}$ is independently hydrogen, or alkyl, or substituted alkyl, or cycloalkyl, or substituted cycloalkyl, cycloalkenyl, or substituted cycloalkenyl, or alkenyl, or substituted cycloalkenyl, or alkynyl, substituted alkynyl, or haloalkyl, or hydroxyalkyl, or alkoxy, or alkoxyalkyl, or heteroalkyl, or haloalkoxy, or aryl, or substituted aryl, or aryloxy, or aralkyloxy, or heteroaryl, or substituted heteroaryl, or heterocycle, or substituted heterocycle, or amino, or alkylamino, or dialkylamino, or hydroxyalkylamino, or (amino)alkyl, or (alkylamino)alkyl, or (dialkylamino)alkyl, or (cyano)alkyl), or carboxamido, or (carboxamido)alkyl, or sulfonamide, or alkylcarbonyl, or arylcarbonyl, or alkylsulfonyl, or arylsulfonyl, or mercaptoalkyl, or carboxy, or carboxyalkyl, or ureido, or guanidine, or (heterocyclo)alkyl, or (heteroaryl)alkyl.

For the purpose of the present disclosure, the term "methacrylamide" as used by itself or as part of another group refers to the radical of formula

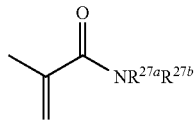

wherein R$^{27a}$ and R$^{27b}$ are independently hydrogen, or alkyl, or substituted alkyl, or cycloalkyl, or substituted cycloalkyl, cycloalkenyl, or substituted cycloalkenyl, or alkenyl, or substituted cycloalkenyl, or alkynyl, substituted alkynyl, or haloalkyl, or hydroxyalkyl, or alkoxy, or alkoxyalkyl, or heteroalkyl, or haloalkoxy, or aryl, or substituted aryl, or aryloxy, or aralkyloxy, or heteroaryl, or substituted heteroaryl, or heterocycle, or substituted heterocycle, or amino, or alkylamino, or dialkylamino, or hydroxyalkylamino, or (amino)alkyl, or (alkylamino)alkyl, or (dialkylamino)alkyl, or (cyano)alkyl), or carboxamido, or (carboxamido)alkyl, or sulfonamide, or alkylcarbonyl, or arylcarbonyl, or alkylsulfonyl, or arylsulfonyl, or mercaptoalkyl, or carboxy, or carboxyalkyl, or ureido, or guanidine, or (heterocyclo)alkyl, or (heteroaryl)alkyl.

For the purpose of the present disclosure, the term "sulfonamido" as used by itself or as part of another group refers to a radical of the formula —SO$_2$NR$^{23a}$R$^{23b}$, wherein R$^{23a}$ and R$^{23b}$ are each independently hydrogen, optionally substituted alkyl, or optionally substituted aryl, or R$^{23a}$ and R$^{23b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "aralkyl" as used by itself or as part of another group refers to an alkyl group substituted with one, two, or three optionally substituted aryl groups. In one embodiment, the aralkyl group is a C$_{1-4}$ alkyl substituted with one optionally substituted aryl group. Non-limiting exemplary aralkyl groups include benzyl, phenethyl, CHPh$_2$, and —CH(4-FPh)$_2$.

For the purpose of the present disclosure, the term "ureido" as used by itself or as part of another group refers to a radical of the formula —NR$^{22a}$C(=O)NR$^{22b}$R$^{22c}$, wherein R$^{22a}$ is hydrogen, alkyl, or optionally substituted aryl, and R$^{22b}$ and R$^{22c}$ are each independently hydrogen, alkyl, or optionally substituted aryl, or R$^{22b}$ and R$^{22c}$ taken together with the nitrogen to which they are attached form a 4- to 8-membered heterocyclo group. Non-limiting exemplary ureido groups include —NHC(C=O)NH$_2$ and —NHC(C=O)NHCH$_3$.

For the purpose of the present disclosure, the term "guanidino" as used by itself or as part of another group refers to a radical of the formula —NR$^{25a}$ C(=NR$^{26}$) NR$^{25b}$R$^{25c}$, wherein R$^{25a}$, R$^{25b}$, and R$^{25c}$ are each independently hydrogen, alkyl, or optionally substituted aryl, and R$^{26}$ is hydrogen, alkyl, cyano, alkylsulfonyl, alkylcarbonyl, carboxamido, or sulfonamido. Non-limiting exemplary guanidino groups include —NHC(C=NH)NH$_2$, —NHC(C=NCN)NH$_2$, —NHC(C=NH)NHCH$_3$, and the like.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a (C$_{1-4}$)alkyl substituted with one optionally substituted heterocyclo group. Non-limiting exemplary (heterocyclo)alkyl groups include:

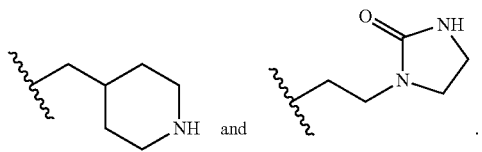 [SMILES: *CC1CCNCC1 ; *CCN1CCNC1=O]

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a (C$_{1-4}$)alkyl substituted with one optionally substituted heteroaryl group. Non-limiting exemplary (heteroaryl)alkyl groups include:

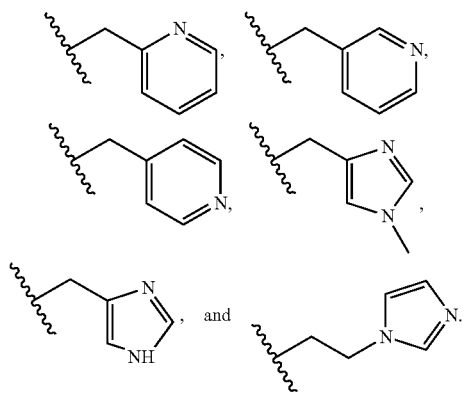

The present disclosure encompasses any of the compounds disclosed herein which are isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^3$H, $^{11}$C, and $^{14}$C. Isotopically-labeled compounds can be prepared by methods known in the art.

Some of the compounds disclosed herein may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The term "about," as used herein in connection with a measured quantity, refers to the normal variations in that measured quantity, as expected by the skilled artisan making the measurement and exercising a level of care commensurate with the objective of measurement and the precision of the measuring equipment.

The term "distal," as used herein refers to the direction of the substrate's surface.

The term "proximal," as used herein refers to the direction of the anti-infective agent.

The term "independently," as used herein in connection with a radical, a molecule, an atom, or any other use is not dependent from anything else. Non-limiting examples is "X$_1$, X$_2$, X$_3$, and X$_4$ are independently non-existent or independently selected from," meaning that X$_1$ can exist, not exist, or be selected from any of the molecules listed, regardless of whether either of X$_2$, X$_3$, and X$_4$ exist, do not exist, or selected from any of the molecules listed, regardless of whether X$_1$, X$_2$, X$_3$, and X$_4$ may be all the same, whether X$_1$, X$_2$, X$_3$, and X$_4$ may all vary, or whether some of X$_1$, X$_2$, X$_3$, and X$_4$ may be the same and some may vary.

The term "radical," as used herein refers to the molecule presented absent a hydrogen, thereby making the molecule available to covalently bind to another molecule, for example to form a brush polymer (in which the molecule structure represents the monomer unit for the brush polymer).

In general, in one or more embodiments, the invention is directed to a composition comprising a functionalized surface of a substrate which is covalently bound to a durable anti-infective agent, such as a quaternary phosphonium compound. In other embodiments, the invention is directed to methods of preparing an anti-infective composition by attaching a durable anti-infective agent, such as a quaternary phosphonium compound to a functionalized surface.

Anti-Infective Composition

Now referring to FIG. 1, substrate's surface 10, in accordance with the present disclosure, is functionalized with a functionalizing layer 20, either natively occurring on the surface or obtained through a functionalizing agent, and an anti-infective agent 30.

Substrates in accordance with the present invention include but are not limited to any device(s) specific to an application by an orthopedic, cardiovascular, plastic, dermatologic, general, maxillofacial or neuro surgeon or physician including, but not limited to, cardiovascular or vascular implant device such as stents, replacement heart valves, replacement heart valve components, leaflets, sewing cuffs, orifices, annuloplasty rings, pacemakers, pacemaker polymer mesh bags, pacemaker leads, pacing wires, intracardiac patches/pledgets, vascular patches, vascular grafts, intravascular catheters, and defibrillators; tissue scaffolds; non-woven meshes, woven meshes, and foams; orthopedic implant devices including orthopedic trauma implants, joint implants, spinal implants, plates, screws, rods, plugs, cages, pins, nails, wires, cables, anchors, scaffolds, artificial joints selected from hand joints, wrist joints, elbow joints, shoulder joints, spine joints, hip joints, knee joints and ankle joints; bone replacement, bone fixation cerclage and dental and maxillofacial implants; spine implant devices including intervertebral cages, pedicle screws, rods, connectors, crosslinks, cables, spacers, facet replacement devices, facet augmentation devices, interspinous process decompression devices, interspinous spacers, vertebral augmentation devices, wires, plates, spine arthroplasty devices, facet fixation devices, bone anchors, soft tissue anchors, hooks, spacing cages, and cement restricting cages; diagnostic implants, biosensors, glucose monitoring devices, external fixation devices, external fixation implants, dental implants, maxillofacial implants, external facial fracture fixation devices and implants, contact lenses, intraocular implants, keratoprostheses; neurosurgical devices and implants selected from shunts and coils; general surgical devices and implants selected from drainage catheters, shunts, tapes, meshes, ropes, cables, wires, sutures, skin and tissue staples, bone anchors, soft tissue anchors, burn sheets, and vascular patches; and temporary/non-permanent implants. Specifically, such devices include an anti-infective agent to counter infective agents.

Surface 10 may be virtually any material which is amenable to either being natively functionalized or to reacting with a functionalizing agent to form a functionalizing layer 20. Examples of such materials include metals, alloys, polymers, plastics, ceramics, silicon, glass, composites, tissue and surfaces with acidic protons, such as —OH or —NH groups.

Metal surfaces which may be employed include titanium and its alloys, stainless steels, cobalt chrome alloys, aluminum, nickel, molybdenum, tantalum, zirconium, hafnium, vanadium, tin, magnesium, manganese, niobium, and alloys containing them; and the like.

Polymer surfaces which may be employed include but not limited to synthetic and/or natural polymer molecules such as: polyamides, polyurethanes, polyureas, polyesters, polyketones, polyimides, polysulfides, polysulfoxides, polysulfones, polythiophenes, polypyridines, polypyrrols, polyethers, polysiloxanes, polysaccharides, fluoropolymers, amides, imides, polypeptides, polyethylene, polystyrene, polypropylene, liquid crystal polymers, thermoplastics, bismalimidtriazine (BT) resins, benzocyclobutene polymers, Ajinomoto Buildup Films (ABF), low Coefficient of Thermal Expansion (CTE) films of glass and epoxies, aramides, polyfluoroolefins, epoxies, silicones or composites containing these polymers.

Functionalizing layer 20 may be any layer suitable for a particular application. In some embodiments, functionalization layer 20 may be native functionalization of the surface. In other embodiments, functionalization layer 20 may be obtained through a functionalizing agent or a plurality of functionalizing agents. In yet other embodiments, functionalization layer 20 may be obtained through a combination of native functionalization and due to a functionalizing agent or a plurality of functionalizing agents. In some embodiments the plurality functionalizing agents may be all identical, all different, or some identical and some different. Such functionalized surfaces can be used to covalently bond subsequent material, such as a linker, a plurality of linkers, layers of anti-infective agent or a plurality of anti-infective agents.

Functionalization of substrate surfaces in accordance with the present invention may be achieved in a variety of ways. For example, it is possible to functionalize the surface of a polymer with an oxide, alkoxide or mixed oxide-alkoxide layer using an alkoxide precursor. In one embodiment, the polymer surface may be coated with a continuous oxide adhesion layer, i.e., a layer that is formed by a matrix of individual spread molecules that are chemically bonded and linked to each other, as opposed to individual molecules sparsely covering the surface. In this embodiment metal alkoxide molecules are bonded together on at least a portion of a polymer surface to form a continuous layer and then converted to an oxide functionalizing layer. In some embodiments, the functionalized surface is coated with a self assembled monolayer (SAM) of functionalizing agent covalently bound to the functionalized surface.

It is further possible to form an adherent coating layer that may be further functionalized with adherent species by heating a self-assembled layer of a functionalized phosphonic acid on the native oxide surface of a substrate. This process, described in detail in U.S. Patent Application Publication 2004/0023048, the entirety of which is incorporated herein by reference, provides on the native oxide surface of a material a multi-segmented, phosphorous-based coating layer having a difunctional organophosphonic acid-based segment bonded to the native oxide surface of the material and a linking segment bonded to the organophosphonic acid-based segment. In accordance with this process, a phosphorous-based coating layer may be provided having a plurality of functionalized organophosphonate moieties bonded to the native oxide surface of a substrate by a phosphonate bond and a plurality of one or more anti-infective coating moieties, each coating moiety being bonded to the functional group of at least one functionalized organophosphonate moiety. When bonded by means of a metal complex, the metal complex is further characterized by being derived from a metal reagent, preferably a metal alkoxide reagent.

The surfaces of the substrates can be further functionalized by a reaction with functionalizing agents such as phosphonic acids, phosphoric acids, carboxylic acids, sulfonic acids, sulfinic acids, phosphonates, phosphonic acid anhydrides, phosphoric acid esters, phosphorus pentoxides, carboxylic acid esters, carboxylic anhydrides, sulfonates, sulfonic acid anhydrides, sulfinic esters, sulfinic anhydrides, alcohols, thiols, alkanes, alkenes, alkynes, and diazo compounds. In some embodiments, a single functionalizing agent is reacted to functionalize the surface. In other embodiments, a plurality of functionalizing agents are reacted to functionalize the surface.

It is yet further possible to covalently bond the anti-infective agent to a functionalizing agent before covalently bonding said functionalized anti-infective agent to a natively functionalized surface, a functionalizing agent bound to a surface, or a linker's distal end. In some embodiments, it is possible to covalently bond a plurality of anti-infective agents to a plurality of functionalizing agents before covalently bonding said plurality of anti-infective agents to a natively functionalized surface, plurality of functionalizing agents bound to the surface, or a plurality of linker's distal ends. In some embodiments, the plurality of anti-infective agents (e.g. quaternary phosphonium compound) may be all identical, all different, or some identical and some different.

Such functionalized surfaces can be used to covalently bond subsequent material or layers thereof on the surface, which in the present invention includes anti-infective agents, or linkers bound to anti-infective agents. A plurality of one or more anti-infective agents may be covalently bonded to the functionalized surface, the functionalizing agents on the surface (which may vary), and the linkers covalently bound to the surface (which may vary).

Anti-infective agents 30 that may be employed may include bactericidal and bacteriostatic agents including disinfectants, antiseptics and antibiotics. Disinfectants include active chlorine such as hypochlorites, chloramines, dichloroisocyanurate and trichloroisocyanurate, wet chlorine, chlorine dioxide and the like, active oxygen, including peroxides, such as peracetic acid, potassium persulfate, sodium perborate, sodium percarbonate and urea perhydrate, iodine compounds such as iodpovidone, iodine tincture, iodinated nonionic surfactants, concentrated alcohols such as ethanol, n-propanol and isopropanol and mixtures thereof; 2-phenoxyethanol and 1- and 2-phenoxypropanols, phenolic compounds, cresols, halogenated phenols, such as hexachlorophene, triclosan, trichlorophenol, tribromophenol, pentachlorophenol, Dibromol and salts thereof, cationic surfactants, including quaternary ammonium cations such as benzalkonium chloride, cetyl trimethylammonium bromide or chloride, didecyldimethylammonium chloride, cetylpyridinium chloride, benzethonium chloride and others, and non-quaternary compounds, such as chlorhexidine, glucoprotamine, octenidine dihydrochloride etc.); strong oxidizers, such as ozone and permanganate solutions; heavy metals and their salts, such as colloidal silver, silver nitrate, mercury chloride, phenylmercury salts, copper, copper sulfate, copper oxide-chloride and the like, and strong acids (phosphoric, nitric, sulfuric, amidosulfuric, toluenesulfonic acids) and alkalis (sodium, potassium, calcium hydroxides).

Organic anti-infective moieties that may be added to a functionalizing layer include quaternary ammonium alkylamines, quaternary ammonium alkanols, usinic acid; cationic peptides such as cecropins neutrophil defensins, polyphemusin, gramicidins, thionins, histone-derived compounds, beta-hairpin, hemoglobin, lactoferrin; anionic peptides such as neuropeptide precursors, aromatic dipeptides, hemocyanin derivatives; other antimicrobial peptides such as bacteriacins, cathelicidin, thrombocidin, and histanins; antibodies, antibiotics, including tetracyclines, amphenicols, penicillins, cephalosporins, monobactams, carbapenems, sulfanomides, trimethoprim, macrolides, streptomycins, quinolones, glycopeptides, polymyxins, lincosamides, streptogramins, imidazole derivatives, nitrofuran derivatives; steroids; chlorhexidine; phenol compounds including triclosan; epoxides; polymers and/or polypeptides which have anti-infective properties.

Inorganic anti-infective coating layers that may be bonded include silver, copper, zinc oxides, titanium oxides, zeolites, silicates, calcium hydroxide, iodine, sodium hypochlorite, sulfites, and sulfates.

Other anti-infective moieties include, quaternary phosphonium compounds, such as Triethyl(12-(methacryloyloxy)dodecyl)phosphonium bromide, quaternary ammonium compounds, such as benzethonium chloride, cetrimonium bromide, cetrimonium chloride, dimethyldioctadecylammonium chloride, tetramethylammonium hydroxide; quaternary ammonium alkyl dendrimers, silver, copper, cationic species such as benzalkonium chloride, Bronidox; and alkylated choline.

In some embodiments the anti-infective agent used is a quaternary phosphonium compound comprising the radical of formula I:

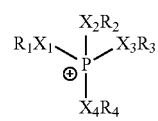

Formula I wherein $X_1$, $X_2$, $X_3$, and $X_4$ are independently non-existent or independently selected from O, S, $NR_5$, =N—, $PR_6$, and =P—; and wherein $R_1$, $R_2$, $R_3$, $R_4$, $R_5$, and $R_6$ are independently selected from the group consisting of hydrogen, alkyls, substituted alkyl, cycloalkyl, substituted cycloalkyl, cycloalkenyl, substituted cycloalkenyl, alkenyl, substituted cycloalkenyl, alkynyl, substituted alkynyl, haloalkyl, hydroxyalkyl, alkoxy, alkoxyalkyl, heteroalkyl, haloalkoxy, aryl, substituted aryl, aryloxy, aralkyloxy, heteroaryl, substituted heteroaryl, heterocycle, substituted heterocycle, amino, alkylamino, dialkylamino, hydroxyalkylamino, (amino)alkyl, (alkylamino)alkyl, (dialkylamino)alkyl, (cyano)alkyl), carboxamido, (carboxamido)alkyl, methacrylate, methacrylamide, sulfonamide, alkylcarbonyl, arylcarbonyl, alkylsulfonyl, arylsulfonyl, mercaptoalkyl, carboxy, carboxyalkyl, ureido, guanidine, (heterocyclo)alkyl, (heteroaryl)alkyl.

In some embodiments, one of $R_1$, $R_2$, $R_3$, or $R_4$ may bind the quaternary phosphonium compound either directly to the functionalized surface, functionalizing agent, or to the distal end of a linker. In other embodiments, more than one of $R_1$, $R_2$, $R_3$, or $R_4$ may bind the quaternary phosphonium compound either directly to a functionalized surface, to a functionalizing agent, or to the distal end of a linker. In some embodiments, $R_1$, $R_2$, $R_3$ and $R_4$ may be the same. In other embodiments, some of $R_1$, $R_2$, $R_3$ and $R_4$ may be the same and some may be different.

In some embodiments, the anti-infective agent used is the radical of the following structure or the monomer of the following structure:

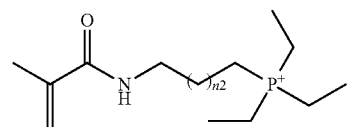

wherein n2 is between 1 and 50.

In one embodiment, the anti-infective agent used is the radical of the following structure or the monomer of the following structure:

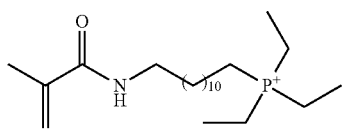

In some embodiments, the anti-infective agent use is the radical of the following structure or the monomer of the following structure:

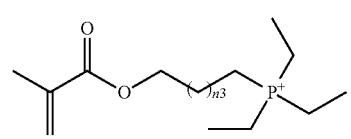

wherein n3 is between 1 and 50.

In one embodiment, the anti-infective agent used is the radical of the following structure or the monomer of the following structure:

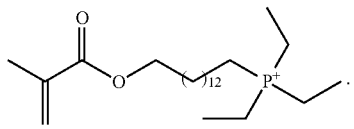

Not all bactericidal and bacteriostatic agents may be used as antiseptics on mammalian tissue as they may have adverse effects thereon. It will be apparent to those skilled in the art that some embodiments of the present invention may apply to uses that do not involve contact of an anti-infective surface with mammalian tissue, such as the fabric used for surgical barriers and the interior surfaces of plumbing fixtures, building materials, ductwork, clean rooms, etc. In such applications certain anti-infective agents may be used, such as disinfectants, which would not be appropriate for use in applications in which contact with mammalian tissue would be contemplated or possible.

In some embodiments anti-infective agents used in applications which involve possible contact with mammalian tissue include but are not limited to quaternary phosphonium compounds such as phosphonium methacrylate, quaternary ammonium compounds such as choline and choline derivatives, quaternary ammonium dendrimers, silver, copper, and cationic species. Quaternary ammonium compounds ("quats") with long alkyl chains show proven biocidal properties by disruption of cell walls. Nakagawa, Y., et al., *Appl. Environ. Microbial.,* 1984, 47:3, 513-518, incorporated by reference herein in its entirety.

In certain embodiments, a linker, having a proximal end and a distal end, may be present between the anti-infective agent and the functionalized surface. In some embodiments, the linker may be covalently bound to the anti-infective agent on its distal end. In some embodiments, the linker may be covalently bound on its proximal end to the functionalized surface, or a functionalizing agent.

In some embodiments, a plurality of linkers, each having a distal and a proximal end, may be covalently bound on their proximal end to a plurality of functionalizing agents or directly to a natively functionalized surface. In some embodiments, a second amount of the plurality of functionalizing agents may remain not bound to the plurality of linkers.

In some embodiments, a plurality of anti-infective agents (such as a quaternary phosphonium compound) may be covalently bound to a plurality of linkers (which are either directly bound to the functionalized surface or are bound to a functionalizing agent). In some embodiments, a second plurality of anti-infective agents (such as a quaternary phosphonium compound) may be covalently bound to the second plurality of functionalizing agents (which previously were not bound to a plurality of linkers).

In certain embodiments, the plurality of linkers may be all identical, all different, or some identical and some different. In certain embodiments, the plurality of functionalizing agents may be all identical, all different, or some identical and some different. In certain embodiments, the plurality of anti-infective agents may be all identical, all different, or some identical and some different.

In some embodiments, the linker may be a radical of the following:

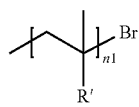

Wherein n1 is between 1 and 100 and R' is independently a hydrogen, or an anti-infective agent (such as a quaternary phosphonium compound).

In certain embodiments, the composition of the present invention has the structure

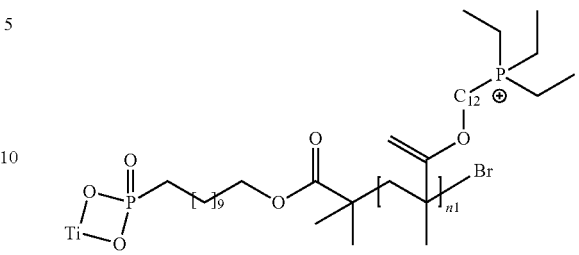

wherein n1 is between 1 and 100.

In certain embodiments, the anti-infective material may be bound to the linker's distal end or to the functionalized surface in a pattern or in a micropattern.

Method for Making an Anti-Infective Composition

Figure 2:
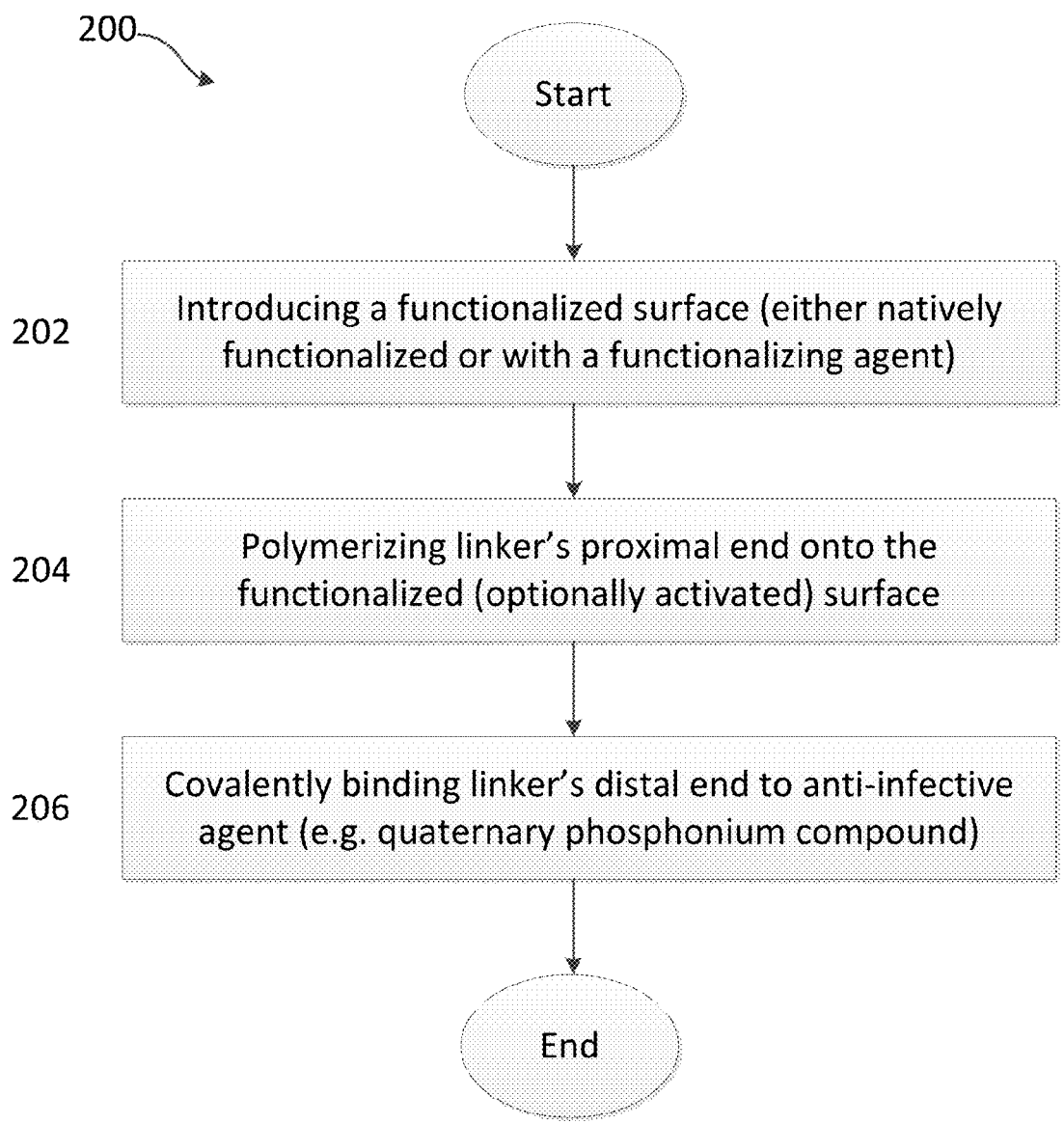
FIG. 2 depicts a flow chart illustrating a method of preparing an anti-infective composition according to an embodiment of the invention.

Now referring to FIG. 2 illustrating a method 200 for making an anti-infective composition according to an embodiment of the invention. In one embodiment, the method comprises attaching an anti-infective agent, such as a quaternary phosphonium compound, to a functionalized surface, which is functionalized either natively or with a functionalizing agent, in accordance with the methods described hereinabove.

In some embodiments, attaching a quaternary phosphonium compound to a functionalized surface comprises: introducing a functionalized surface pursuant to block 202 (functionalized either natively or with a functionalizing agent, in accordance with the methods described hereinabove), optionally activating the functionalized surface (not shown), polymerizing a linker, having a proximal and a distal end, to form a covalent bond between the activated functionalized surface and the proximal end of the linker pursuant to block 204, and subsequently covalently binding the distal end of the linker to the quaternary phosphonium compound anti-infective agent (which may be functionalized and/or activated) pursuant to block 206.

Figure 3:
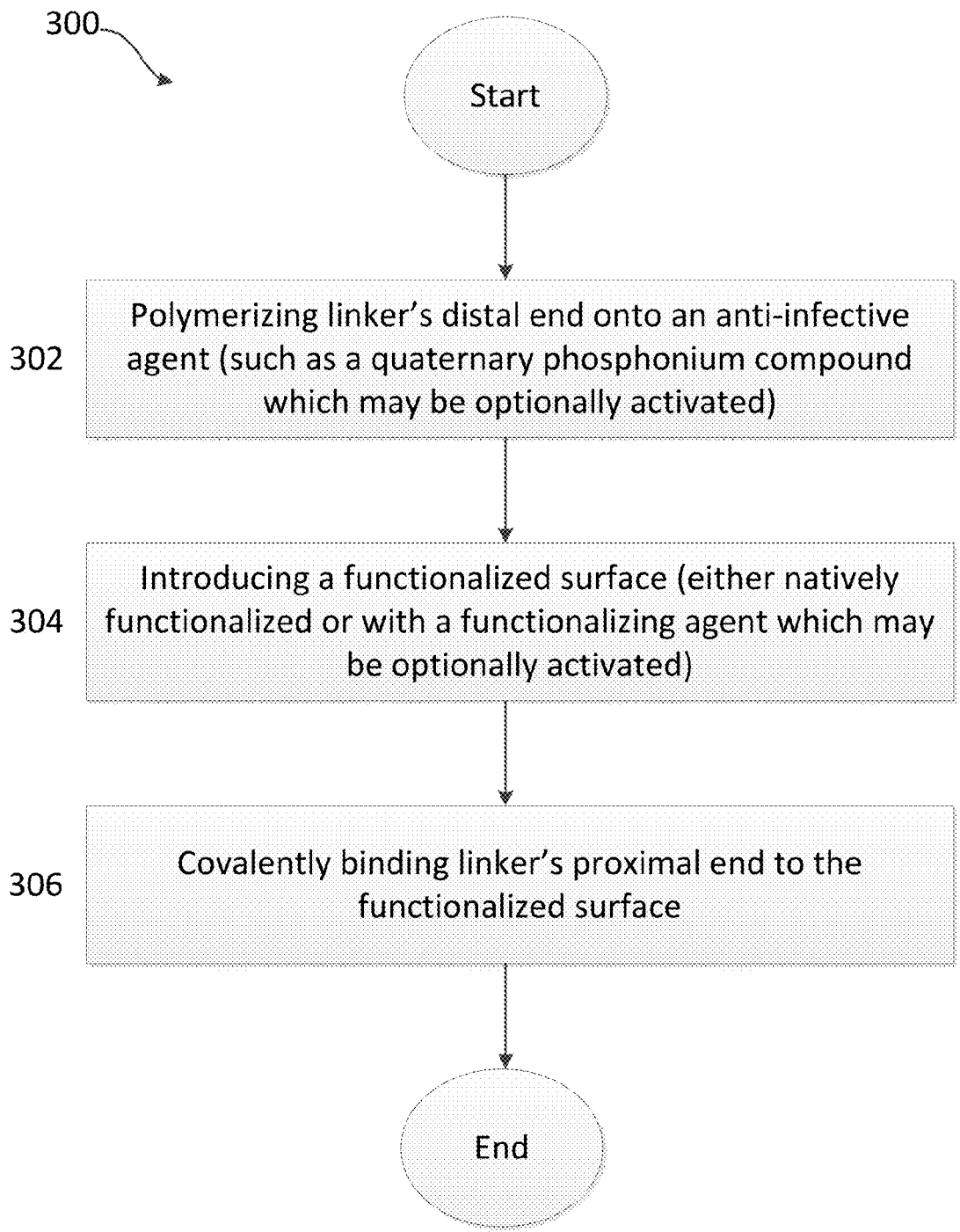
FIG. 3 depicts a flow chart illustrating a method of preparing an anti-infective composition according to another embodiment of the invention.

In other embodiments, as illustrated in FIG. 3 by method 300, the order may vary. For example, attaching a quaternary phosphonium compound to a functionalized surface may comprise: polymerizing a linker, having a proximal and a distal end, to form a covalent bond between the anti-infective agent (e.g., quaternary phosphonium compound) and the distal end of the linker pursuant to block 302, introducing a functionalized surface pursuant to block 304 (functionalized either natively or with a functionalizing agent, in accordance with the methods described hereinabove), optionally activating the functionalized surface (not shown), and subsequently covalently binding the proximal end of the linker to the functionalized surface pursuant to block 306.

In yet other embodiments, attaching a quaternary phosphonium compound to a functionalized surface may comprise: polymerizing a linker, having a proximal and a distal end, to form a covalent bond between the quaternary phosphonium compound and the distal end of the linker; and simultaneously covalently binding the proximal end of the linker to the functionalized surface.

In some embodiments, covalently bonding the linker may comprise using Surface-Initiated Atom Transfer Radical Polymerization (SI ATRP). In some embodiments polymerizing through SI ATRP comprises: introducing an anti-infective agent (e.g., quaternary phosphonium compound), introducing an initiator (e.g., alkyl halide initiator), introducing a transition metal complex (e.g., CuBr), introducing a ligand (e.g., N,N,N',N'',N''''-pentamethyldiethylenetriamine), and polymerizing for a predetermined time to obtain a desired polymer brush thickness.

In some embodiments, the ratio of the components in the polymerization step is 2:1:1.4 of monomer:metalcomplex:ligand. In some embodiments, the polymer brush thickness effects the antibacterial efficacy. In some embodiments, the composition disclosed herein shows greater than 99% reduction in a variety of bacteria for prolonged duration.

It is believed that one of ordinary skill in the art can, using the preceding description and the following illustrative examples, make and utilize the compounds and articles of the present invention and practice the claimed methods. The following examples are given to illustrate the present invention. It should be understood that the invention is not to be limited to the specific conditions or details described in these examples.

Example 1: Synthesis of Antibacterial Polymer Brushes Via Surface-Initiated Atom Transfer Radical Polymerization (SI-ATRP)

Figure 4:
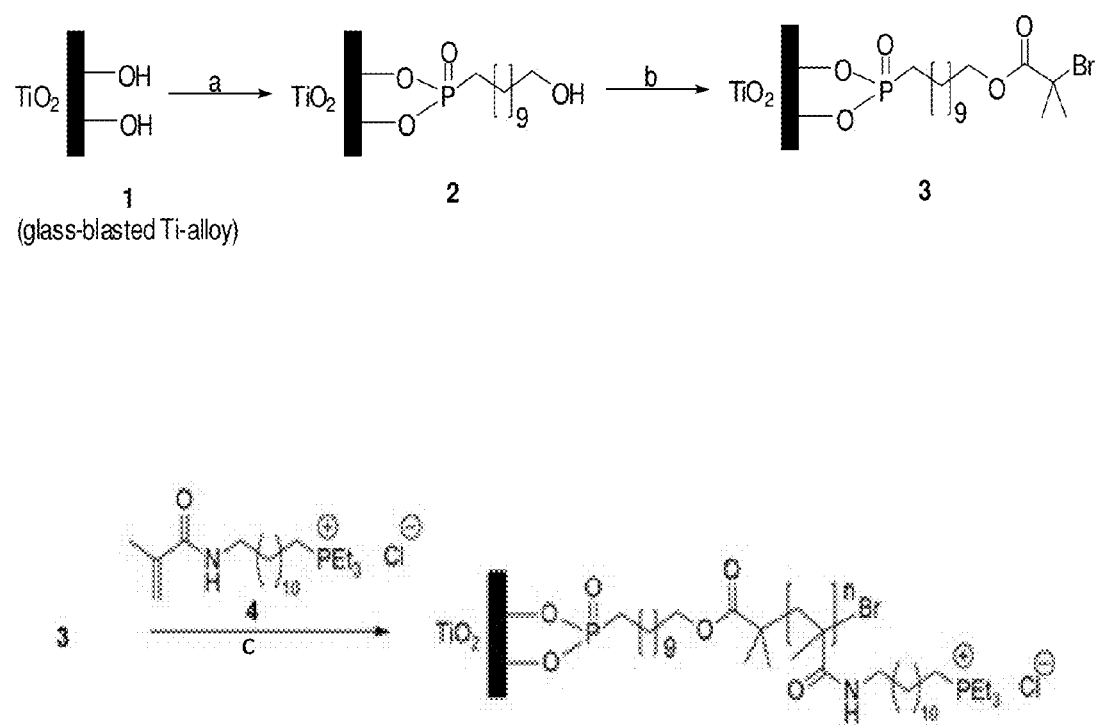
FIG. 4 depicts a scheme illustrating a method of preparing a particular anti-infective composition pursuant to example 1.

Referring to FIG. 4, glass bead-blasted Ti-alloy ($Ti_6V_aAl$) coupons 1 were cleaned and contacted with phosphonoundecanol (PUL) in a 15 mM solution of PUL in ethanol, thereby covalently binding the PUL to the titanium alloy, and forming a Self Assembled Monolayer (SAM) of PUL on the titanium alloy surface as illustrated by numeral 2. Step a is also referred to, in some embodiments of the invention, as covalently binding a functionalizing agent to the surface, where the functionalizing agent in this instance is PUL.

The terminal hydroxyl group of the functionalizing agents 2 (PUL) were esterified with α-bromoisobutyryl bromide in dichloromethane to form the composition illustrated by numeral 3. Step b is also referred to, in some embodiments of the invention, as activating the surface, thereby preparing it for subsequent SI-ATRP of the linker (i.e. covalently binding the linker on its proximal end to the surface) and ultimately of the anti-infective (i.e. covalently binding the anti-infective agent to the linker on its distal end).

The SI-ATRP of the anti-infective agent, quaternary phosphonium compound phosphonium methaceylate illustrated by numeral 4, was performed in water in the presence of CuBr and a ligand N,N,N',N'',N''-pentamethyldiethylenetriamine (PMDETA). The ratio employed was [monomer]:[Cu]:[PMDETA]=2:1.0:1.4. However, one of ordinary skill in the art will appreciate that the polymerization time and amount of monomer used may vary to control the thickness of the polymer brushes and the resulting antibacterial properties of polymer brush surfaces. Step c is also referred to, in some embodiments of the invention, as polymerizing a linker onto the activated functionalized surface and covalently binding the quaternary phosphonium compound to the linker.

Figure 5:
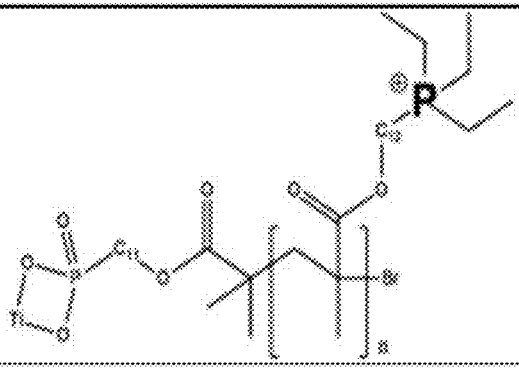
FIG. 5 depicts the anti-bacterial efficacy of two anti-infective compositions prepared pursuant to some embodiments of the invention immediately after the compositions were prepared (t=0).

FIG. 5 illustrates the prolonged antibacterial performance of the composition prepared according to embodiments of the invention. A composition comprising a radical of the quaternary phosphonium compound of the following structure:

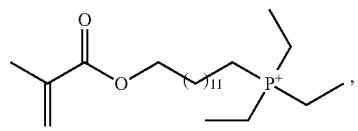

have shown a 99.5% killing of S. aureus and a 98% of E. coli. Additionally, a composition comprising a radical of the quaternary phosphonium compound of the following structure:

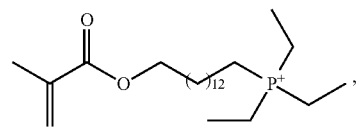

have shown a 98.9% killing of S. aureus and a 99% of E. coli.

Figure 6:
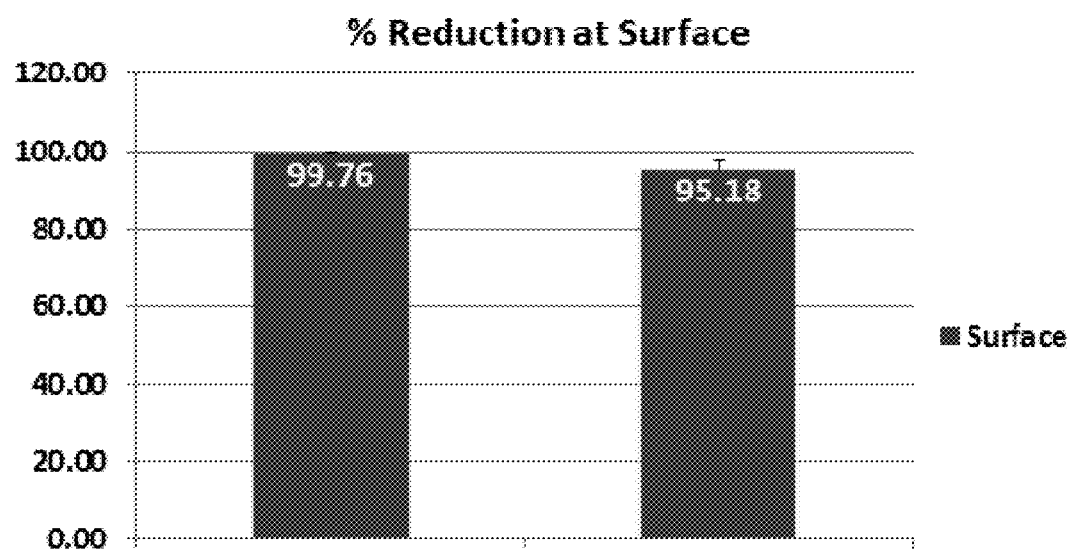
FIG. 6 depicts the anti-bacterial efficacy of two anti-infective compositions prepared pursuant to some embodiments of the invention one year after the compositions were prepared (t=1 year).
Figure 6:
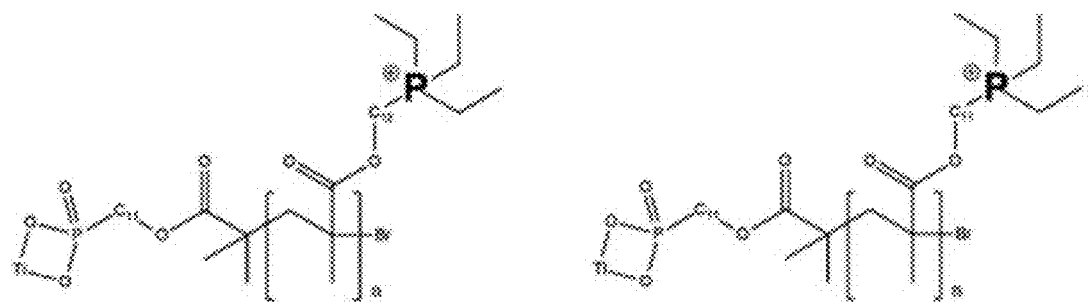

The antibacterial activity and efficacy was shown to be maintained even after aging the composition for one year as6 illustrated in FIG. 6. Test coupons were placed in a modified ASTM E2149 efficacy study using S. aureus (ATCC#29213) with an inoculum level of $10^6$ Colony Forming Units (CFU) per ml. After a 24 hour exposure, the coupons were evaluated relative to untreated samples for CFU/ml reduction from bacteria recovered directly from the sample surface, and showed >95% killing at the surface for both treatments. Specifically, a 95.2% killing was observed at the titanium surface treated with the quaternary organophosphonate compound of the following structure:

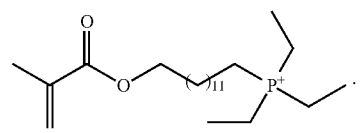

No reduction in antibacterial efficacy was observed outside of the margin of error of the experiment. In changes in the antibacterial efficacy are likely due to variability in the treatment and the essay rather that real reduction in efficacy over time. Additionally, a 99.8% killing was observed at the titanium surface treated with the quaternary organophosphonate compound of the following structure:

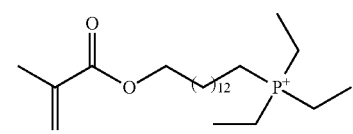

Similarly to the previous compound, no reduction in antibacterial efficacy was observed outside of the margin of error of the experiment. In changes in the antibacterial efficacy are likely due to variability in the treatment and the essay rather that real reduction in efficacy over time.

Example 2: Synthesis of a Quaternary Phosphonium Compound Phosphonium Methacrylate A 100 mL pressure tube was charged successively with acetonitrile (18 mL), triethylphosphine (2.05 mL, 17.3 mmol) and 12-bromo-1-dodecanol (4.00 g, 15.1 mmol). The mixture was heated at 90° C. for 2 days and concentrated in vacuum. The residue was dissolved in dichloromethane (10 mL). The solution was added drop-wise into ether (150 mL) with stirring to precipitate the product. After stirring for an additional one hour, the precipitates were collected by filtration, washed with ethanol, and air-dried to afford the target compound, i.e. Triethyl(12-hydroxydodecyl)phosphonium bromide (4.4 g, 65%).

To a solution of triethyl(12-hydroxydodecyl)phosphonium bromide (4.00 g, 10.4 mmol) in chloroform (50 mL) was slowly added methacryloyl chloride (1.07 mL, 11.0 mmol) at 0° C. and the mixture was stirred at room temperature for three days. Upon completion, the mixture was diluted with dichloromethane. Sodium carbonate (5 g) was added to the mixture. After stirring for 30 min, the mixture was filtered and concentrated in vacuum. The residual oil was then passed through a fritted glass filter to afford the product, i.e. Triethyl(12-(methacryloyloxy)dodecyl)phosphonium bromide (4.7 g, quantitative).

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law. All references cited herein are incorporated fully by reference.

What is claimed is:

1. A composition comprising:
   a substrate comprising a functionalized surface; and
   a quaternary phosphonium compound bonded to the functionalized surface, wherein the quaternary phosphonium compound is a radical of:

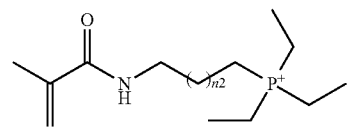

wherein n2 is between 1 and 50.

2. The composition of claim 1, wherein the functionalized surface is natively functionalized or functionalized with a functionalizing agent covalently bonded thereto.

3. The composition of claim 2, further comprising a linker, having a proximal end and a distal end, wherein the linker is covalently bonded on its proximal end to the natively functionalized surface, and wherein the linker is covalently bonded on its distal end to the quaternary phosphonium compound.

4. The composition of claim 2, further comprising a linker, having a proximal and a distal end, wherein the linker is covalently bonded on its proximal end to the functionalizing agent, and wherein the linker is covalently bonded on its distal end to the quaternary phosphonium compound.

5. The composition of claim 1, wherein the functionalized surface is selected from the group consisting of metals, alloys, polymers, plastics, ceramics, silicon, glass, composites, tissue and surfaces with acidic protons.

6. The composition of claim 2, wherein the functionalized surface is functionalized with a functionalizing agent selected from the group consisting of phosphonic acids, phosphoric acids, carboxylic acids, sulfonic acids, sulfinic acids, phosphonates, phosphonic acid anhydrides, phosphoric acid esters, phosphorus pentoxides, carboxylic acid esters, carboxylic anhydrides, sulfonates, sulfonic acid anhydrides, sulfinic esters, sulfinic anhydrides, alcohols, thiols, alkanes, alkenes, alkynes, and diazo compounds.

7. The composition of claim 4, wherein the linker has the structure:

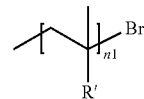

wherein n1 is between 1 and 100 and R' is independently a hydrogen, or a quaternary phosphonium compound.

8. A composition comprising:
   a substrate comprising a functionalized surface; and
   a quaternary phosphonium compound bonded to the functionalized surface, wherein the composition has a structure:

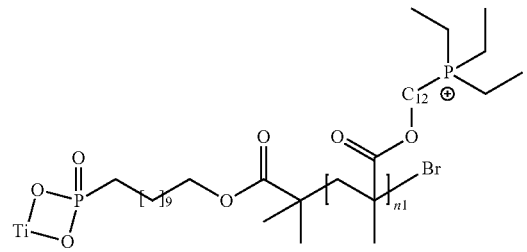

wherein n1 is between 1 and 100.

9. A method for preparing a composition comprising:
attaching a quaternary phosphonium compound to a functionalized surface of a substrate, wherein the quaternary phosphonium compound has a radical of formula I:

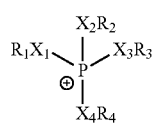

Formula I wherein $X_1$, $X_2$, $X_3$, and $X_4$ are independently nonexistent or independently selected from O, S, $NR_5$, =N—, $PR_6$, and =P—; and
wherein $R_1$, $R_2$, $R_3$, $R_4$, $R_6$, and $R_6$ are independently selected from the group consisting of hydrogen, alkyls, substituted alkyl, cycloalkyl, substituted cycloalkyl, cycloalkenyl, substituted cycloalkenyl, alkenyl, substituted cycloalkenyl, alkynyl, substituted alkynyl, haloalkyl, hydroxyalkyl, alkoxy, alkoxyalkyl, heteroalkyl, haloalkoxy, aryl, substituted aryl, aryloxy, aralkyloxy, heteroaryl, substituted heteroaryl, heterocycle, substituted heterocycle, amino, alkylamino, dialkylamino, hydroxyalkylamino, (amino)alkyl, (alkylamino)alkyl, (dialkylamino)alkyl, (cyano)alkyl), carboxamido, (carboxamido)alkyl, methacrylate, methacrylamide, sulfonamide, alkylcarbonyl, arylcarbonyl, alkylsulfonyl, arylsulfonyl, mercaptoalkyl, carboxy, carboxyalkyl, ureido, guanidine, (heterocyclo)alkyl, and (heteroaryl)alkyl, and are linked to the phosphorus through any one of oxygen, nitrogen, sulfur, carbon, and phosphorus;
wherein attaching the quaternary phosphonium compound comprises polymerizing a linker, having a proximal end and a distal end, to form a covalent bond between the quaternary phosphonium compound and the distal end of the linker; and subsequently covalently bonding the proximal end of the linker to the functionalized surface.

10. The method of claim 9, wherein attaching the quaternary phosphonium compound to a functionalized surface comprises:
covalently bonding a functionalizing agent to the surface; and
covalently bonding the quaternary phosphonium compound to the functionalized surface.

11. The method of claim 9, wherein the functionalized surface is selected from the group consisting of metals, alloys, polymers, plastics, ceramics, silicon, glass, composites, tissue and surfaces with acidic protons.

12. The method of claim 10, wherein the functionalizing agent is selected from the group consisting of phosphonic acids, phosphoric acids, carboxylic acids, sulfonic acids, sulfinic acids, phosphonates, phosphonic acid anhydrides, phosphoric acid esters, phosphorus pentoxides, carboxylic acid esters, carboxylic anhydrides, sulfonates, sulfonic acid anhydrides, sulfinic esters, sulfinic anhydrides, alcohols, thiols, alkanes, alkenes, alkynes, and diazo compounds.

13. A method for preparing a composition comprising:
attaching a quaternary phosphonium compound to a functionalized surface of a substrate, wherein the quaternary phosphonium compound is a radical of the following:

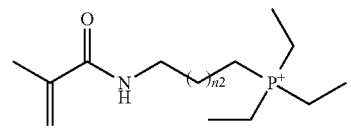

wherein n2 is between 1 and 50.

14. The method of claim 9, wherein the linker has a structure:

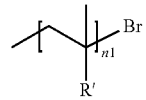

wherein n1 is between 1 and 100 and R' is independently a hydrogen, or a quaternary phosphonium compound.

15. A method for preparing a composition comprising:
attaching a quaternary phosphonium compound to a functionalized surface of a substrate, wherein the composition has a structure:

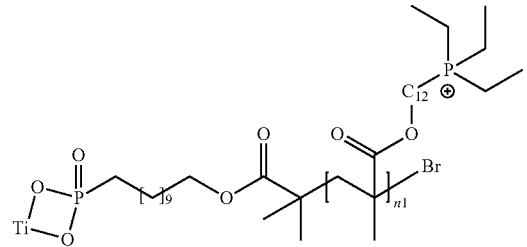

wherein n1 is between 1 and 100.

16. A method for preparing a composition comprising:
attaching a quaternary phosphonium compound to a functionalized surface of a substrate, wherein the quaternary phosphonium compound is a radical of the following:

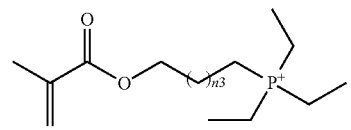

wherein n3 is between 1 and 50.

* * * * *